(12) United States Patent
Maekawa

(10) Patent No.: US 7,029,884 B2
(45) Date of Patent: Apr. 18, 2006

(54) CARRIER FOR MICROORGANISM INCUBATION IN WHICH MICRO-ELEMENTS AND INORGANIC NUTRIENT SALTS ARE DIFFUSED

(75) Inventor: Takaaki Maekawa, Tsukuba (JP)

(73) Assignee: Japan Science and Technology Corporation, Saitama (JP)

( * ) Notice: Subject to any disclaimer, the term of this patent is extended or adjusted under 35 U.S.C. 154(b) by 34 days.

(21) Appl. No.: 10/419,161

(22) Filed: Apr. 21, 2003

(65) Prior Publication Data

US 2004/0018609 A1 Jan. 29, 2004

Related U.S. Application Data

(63) Continuation of application No. 09/851,106, filed on May 9, 2001, now abandoned, which is a continuation of application No. 09/638,957, filed on Aug. 16, 2000, now abandoned, which is a continuation of application No. 09/086,714, filed on May 29, 1998, now abandoned.

(30) Foreign Application Priority Data

May 29, 1997 (JP) .................................. 97-140181

(51) Int. Cl.
*C12P 5/00* (2006.01)
*C12P 3/00* (2006.01)
*C12P 11/14* (2006.01)
*C12P 11/08* (2006.01)
*C12P 1/00* (2006.01)

(52) U.S. Cl. ....................... 435/166; 210/601; 435/176; 435/180; 435/262.5; 435/289.1

(58) Field of Classification Search ................ 435/176, 435/180, 166, 262.5, 289.1; 210/601
See application file for complete search history.

(56) References Cited

U.S. PATENT DOCUMENTS

| | | | | |
|---|---|---|---|---|
| 3,928,191 A | * | 12/1975 | Belasco | 210/612 |
| 4,230,806 A | * | 10/1980 | Nojiri et al. | 435/71.1 |
| 5,100,553 A | * | 3/1992 | Nomura et al. | 210/610 |
| 5,518,890 A | | 5/1996 | Starkweather et al. | |
| 5,616,241 A | * | 4/1997 | Khudenko | 210/151 |
| 5,844,068 A | * | 12/1998 | Otera et al. | 528/361 |
| 5,874,165 A | | 2/1999 | Drumheller | |

FOREIGN PATENT DOCUMENTS

| | | |
|---|---|---|
| JP | 62-236484 | 10/1987 |
| JP | 2-5852 | 1/1990 |

* cited by examiner

*Primary Examiner*—David M. Naff
(74) *Attorney, Agent, or Firm*—Wenderoth, Lind & Ponack, L.L.P.

(57) ABSTRACT

A carrier for microorganism incubation of a diffusion type in which microelements and inorganic nutrient salts which are useful in proliferation of microorganism are included in a porous material is provided. This carrier may be employed in a bioreactor for treatment of waste water where high activity and high density of the microorganism is desired.

11 Claims, 16 Drawing Sheets

Carrier (A)

Carrier (B)

Carrier (C)

Fluidized-bed bioreactor

Fixed-bed bioreactor

Apparatus by intermittent aerative nitration and denitration

Daily change in methane production under various concentrations of micrometal salts (microorganism density : 0.6 g/liter)

Influence of pH on the rate of hydrogen production by hydrogen-productive microorganism

CARRIER FOR MICROORGANISM INCUBATION IN WHICH MICRO-ELEMENTS AND INORGANIC NUTRIENT SALTS ARE DIFFUSED

This is a continuation of Ser. No. 09/851,106, filed May 9, 2001, now abandoned, which is a continuation of Ser. No. 09/638,957, filed Aug. 16, 2001, now abandoned, which is a continuation of Ser. No. 09/086,714, filed May 29, 1998, now abandoned.

FIELD OF THE INVENTION

The present invention relates to a carrier for microorganism incubation wherein microelements and inorganic nutrients are diffused. More particularly, it relates to a carrier for microorganism incubation of a type wherein microelements and inorganic nutrients are diffused and which in useful for apparatus in treating waste water, food manufacturing industry, pharmaceutical manufacturing industry, etc.

PRIOR ART AND PROBLEMS THEROF

With regard to a means for the manufacture of carrier, a method where microorganism or enzyme is included in a high-molecular polymer gel (an inclusion method) has been known already and utilized in an industrial scale.

However, in a conventional method as such, micrometal elements and inorganic nutrient salts which are useful for proliferation of microorganism depend upon their diffusion and movement from the external medium to the inner part of the carrier and, therefore, the diffusing rate of those substances is dependent upon the proliferation of the microorganism. In addition, the metabolized substances have a diffusion resistance to the carrier surface whereby they may disturb the proliferation of the microorganism. Further, when gaseous substance is metabolized, floating and destruction of the carrier take place. Furthermore, in the conventional means such as an inclusion method, there is a problem that activity of the microorganism significantly decreases due to toxicity of the high-molecular substance used and, accordingly, even when density of the microorganism increases, activity of the microorganism is not always proportional to the density of the microorganism.

In order to solve such a problem, a carrier of a surface binding type whereby microorganism is physicochemically adhered to the carrier has been developed.

However, that method depends upon the physicochemical adhesion of a sticky high-molecular substance which is secreted upon proliferation of the microorganism to the carrier and, therefore, proliferating rate of the microorganism is dependent upon the constitution of inorganic nutrient salts and microelement components impregnated from an external liquid. Further, there is an additional problem that, when the microorganism existing on the surface of the carrier flows within a bioreactor, exfoliation of the microorganism takes place whereby there is an inherent limitation in the high-density enrichment incubation.

Under such circumstances, an object of the invention of this application is to offer a carrier for microorganism incubation of a new type in which microelements and inorganic nutrient salts are diffused whereby high activity and high density of the microorganism can be achieved in a bioreactor and in an apparatus for treating waste water.

SUMMARY OF THE INVENTION

The present invention is to solve the above-mentioned problems and to offer a carrier for microorganism incubation in which microelements and inorganic nutrient salts are diffused, characterized in that, the microelements and the inorganic nutrients salts which are useful for proliferation of lthe microorganism are included in a porous material.

This invention further offers a carrier for microorganism incubation wherein organic carbon sources such as glucose and biodegradable resin are included in the above-mentioned carrier; a carrier for microorganism incubation wherein the microorganism is included in the above-mentioned carrier; a carrier for microorganism incubation according to each of the above wherein the surface is coated with a high-molecular polymer; a carrier for microorganism incubation according to each of the above wherein the microorganism is subjected to an enrichment proliferation on the surface thereof followed by being coated with the high-molecular polymer again; a carrier for microorganism incubation coated with a biodegradable resin; a carrier for microorganism incubation wherein the high-molecular polymer coat contains magnetic powder; etc.

This invention furthermore offers a carrier for microorganism incubation wherein the porous material is a high-molecular polymer or gel of a high-molecular polymer; a carrier for microorganism incubation wherein the porous material is ceramics or natural stone material; and a carrier for microorganism incubation wherein the high-molecular polymer is included in the high-molecular polymer gel.

This invention also provides a carrier for microorganism incubation comprising of a rock wool as a porous material: and the carrier thereof for a fixed-bed type methane fermentation.

BRIEF EXPLANATION OF THE DRAWINGS

and each of (A) and (B) of FIG. 13 is a graph which shows an example of influence of pH on the rate of hydrogen production

EMBODIMENTS OF THE INVENTION

Figure 1:
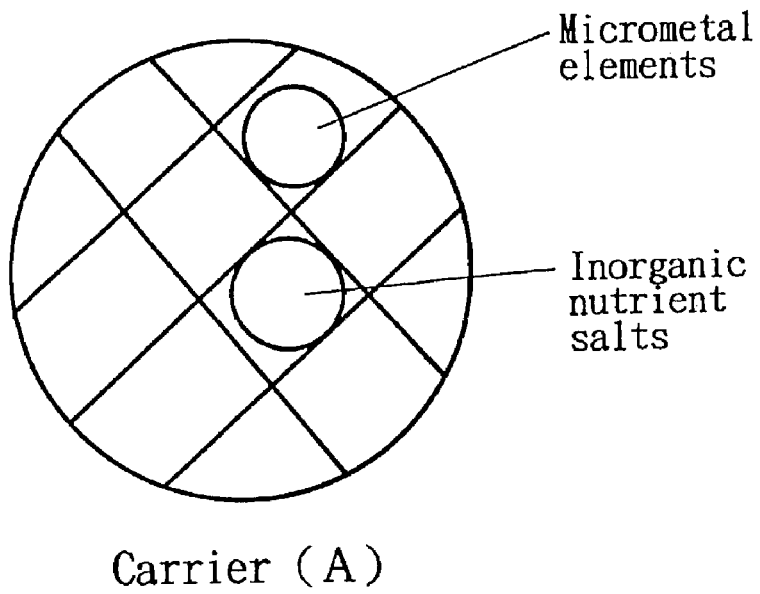
FIG. 1 is a drawing which exemplifies the carrier (A) of this invention.

In the invention of this application, as a carrier of a bonded type as mentioned above, the substances useful for proliferation of microorganism such as microelements and inorganic nutrient salts are included in a carrier of a bonded type in high concentrations. As a result thereof, a decrease in the activity of the microorganism due to toxicity of the porous material such as the high-molecular polymer used there can be prevented and, in addition, inhibition of the proliferation can be prevented by adjusting the thickness and the gap of the high-molecular polymer which constitutes the carrier used. Further, the surface is coated for preventing the physical exfoliation of the microorganism which is proliferated on the carrier surface whereby the exfoliation of the microorganism can be prevented corresponding to the microorganism species and characteristics thereof as well as to the fluidizing method of the reactors.

Furthermore, this invention is derived from the finding on a study of high-concentration incubation of methane bacteria using oxygen and hydrogen as substrates, that is, from a finding that, since a deficiency in microelements and inorganic nutrient salts necessary for proliferation of microorganism determines the proliferation rate of the microorganism, supply of a substance which restricts the proliferation is able to make the density of the microorganism high.

Still further, the above finding is in accord with Liebig's minimum principle that, in any microorganisms, proliferation of microorganism ceases when even one of the substances necessary for the microorganism is deficient. From this finding, a method of supplying a substance which is necessary for proliferation of various microorganisms being in activity in a bioreactor or in a treating apparatus for waste water is that such a substance is included in the carrier in a high concentration, diffused and moved onto the surface from the inner side of the carrier by means of diffusion and supplied to the microorganism living on the surface. It has been ascertained by experiments that, when the microorganism incorporates said substance therein, proliferation continues whereby the state of high density of the microorganism can be maintained.

In the carrier of this invention in which microelements and inorganic nutritive salts are included, gel or the like consisting of high-molecular polymer is used as a porous material and the microelements and the inorganic nutrient salts are immobilized in said gel. With regard to a porous material itself however, it may consist of various kinds of porous high-molecular polymer, gel of high-molecular polymer or accumulate of fine particles of polymer or, further, it may be porous ceramics or natural stone materials such as pumice stone.

With regard to high-molecular polymer or gel thereof, representative examples are various polymers or copolymerized polymers known as water-absorbing polymer, etc. such as those of acryl type, methacryl type, vinyl alcohol type, vinyl ester type, polyether type, polyester type and polyolefin type.

The microorganism per se is bonded with and immobilized in the carrier of this invention having the above-mentioned porous material by, for example, means of covalent bond, physical adsorption or ionic bond on the surface, in the pores inside, in the gaps, etc. The microorganism may be included in the carrier or may be accumulated on the carrier surface only or both types may be coexisting.

The high-molecular polymer which coats the surface has a role of controlling the diffusion of microelements and inorganic nutrient salts included in the porous material as well as organic carbon source such as glucose and biodegradable resin to a necessary extent. Due to its gradual decomposition, the biodegradable resin is designed to supply the organic carbon source to the microorganism.

Figure 2:
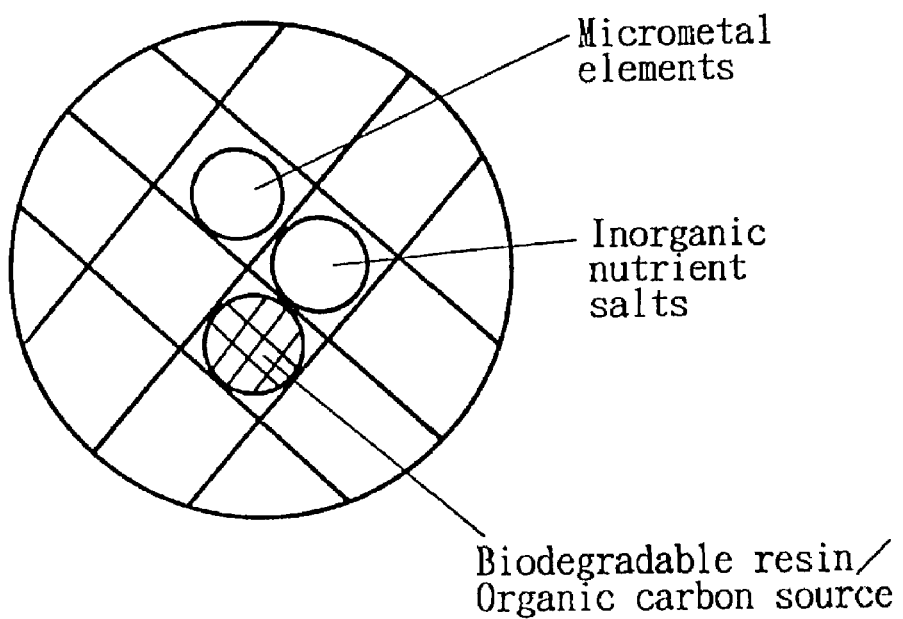
FIG. 2 is a drawing which shows an example where biodegradable resin/organic carbon source are carried on the carrier (A)
Figure 3:
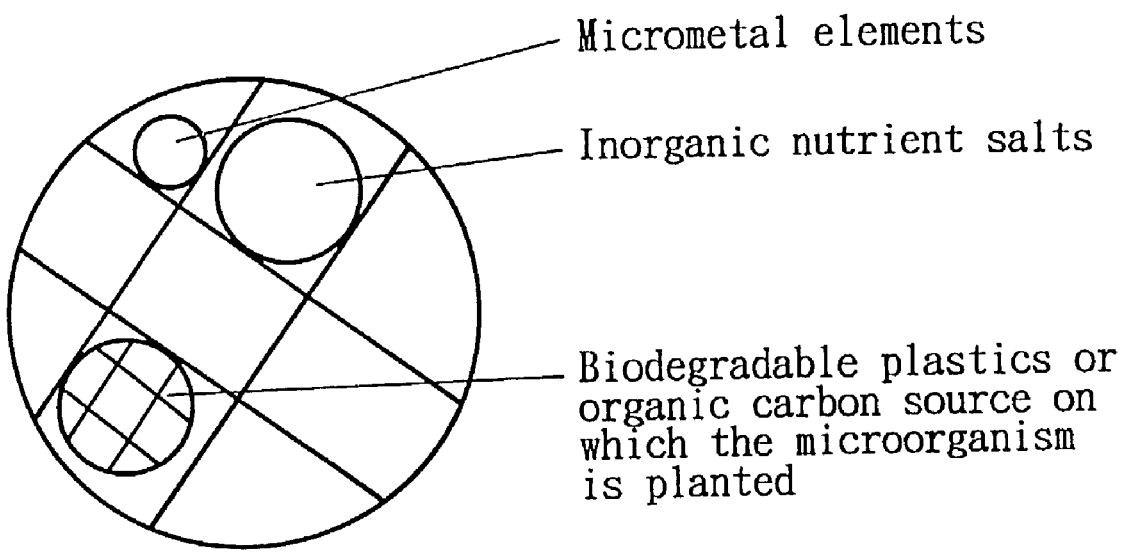
FIG. 3 is a drawing which shows an example where the microorganism is planted in biodegradable resin and organic carbon source.

This invention will be illustrated using some models by means of drawings. First, the basic constitution of this invention can be given as in FIG. 1. A carrier for microorganism incubation (A) is constituted in such a manner that microelements and inorganic nutrient salts are included and carried in a porous material such as a high-molecular polymer ge. FIG. 2 shows a carrier (A) where organic carbon source and biodegradable resin are further included. FIG. 3 shows an example of a carrier (A) where the microorganism is included or, for example, the microorganism is planted on biodegradable plastics or organic carbon source.

Figure 4:
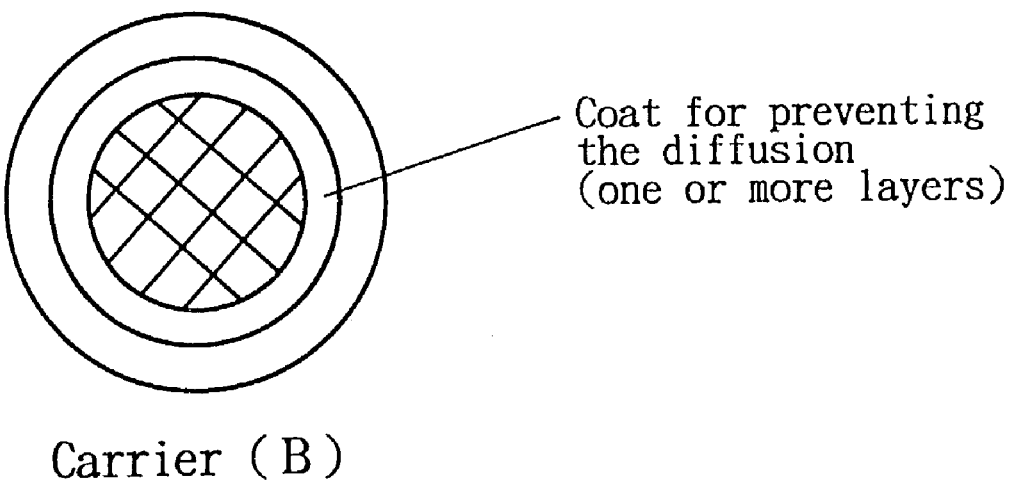
FIG. 4 is a drawing which shows a carrier (B) having a coat for controlling the diffusion.

FIG. 4 shows an example of a carrier (B) of this invention according to any of the above-mentioned carriers where one or more layer(s) of coating for controlling the diffusion is/are formed by a high-molecular polymer on the surface.

Figure 5:
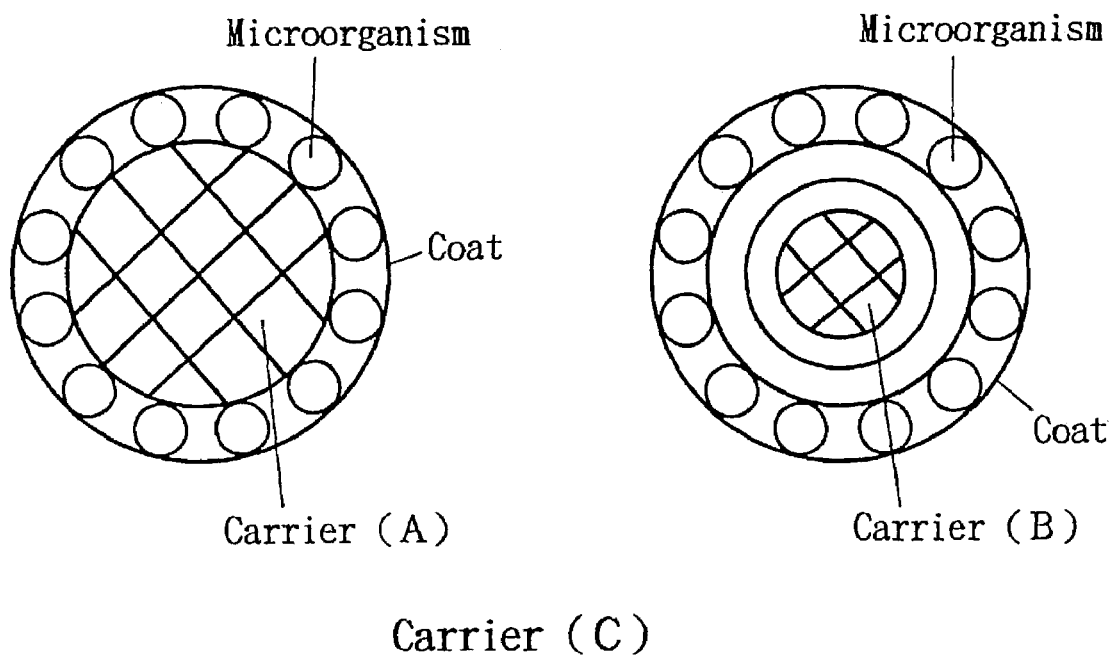
FIG. 5 is a drawing which shows a carrier (C) having a coat on the microorganisms on the surface.
Figure 6:
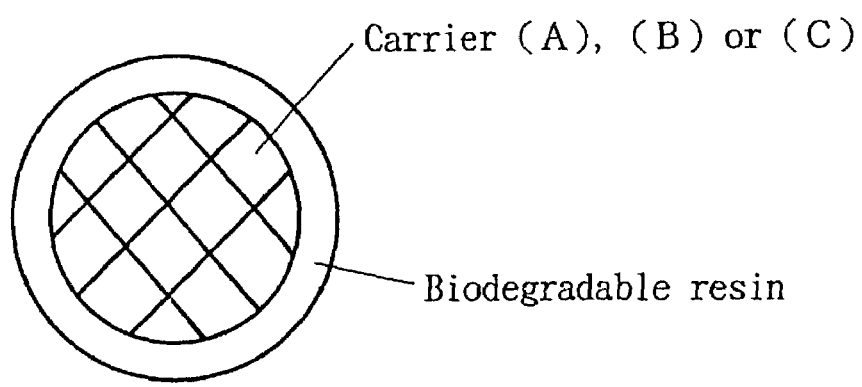
FIG. 6 is a drawing which shows an example where biodegradable resin is coated on any of the carriers (A), (B) and (C)

FIG. 5 shows an example of a carrier (C) of this invention according to each of the above-mentioned carriers (A) and (B) where the microorganism is accumulated on the surface and then a high-molecular polymer is placed as a coating thereon. FIG. 6 is an example of a carrier of this invention according to any of the carriers (A), (B), and (C) where a biodegradable resin is further coated.

Figure 7:
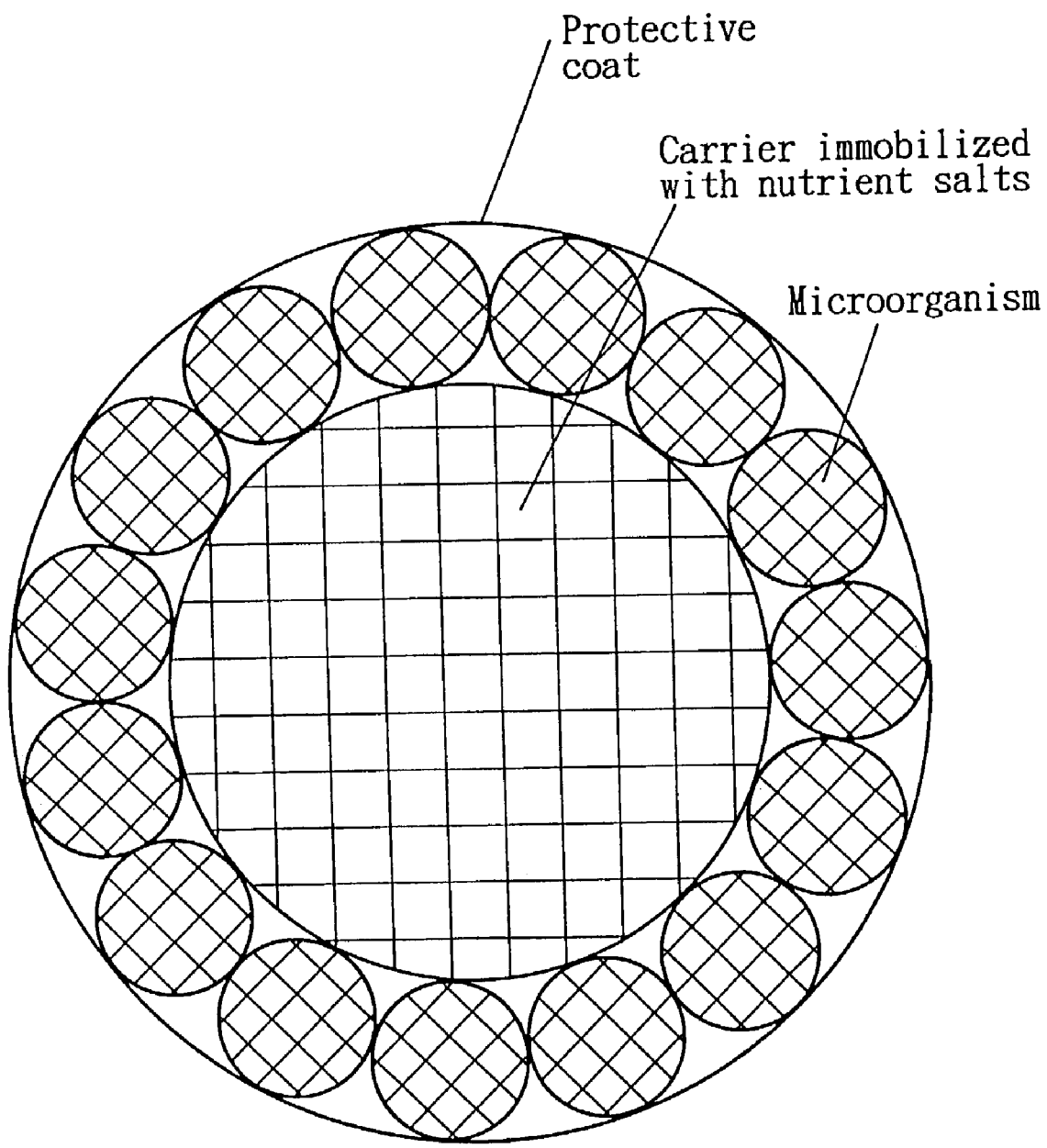
FIG. 7 is a drawing which shows the drawing of FIG. 5 as an enlarged model.

FIG. 7 is an example of a model of the example mentioned as FIG. 5 in an enlarged manner.

Figure 8:
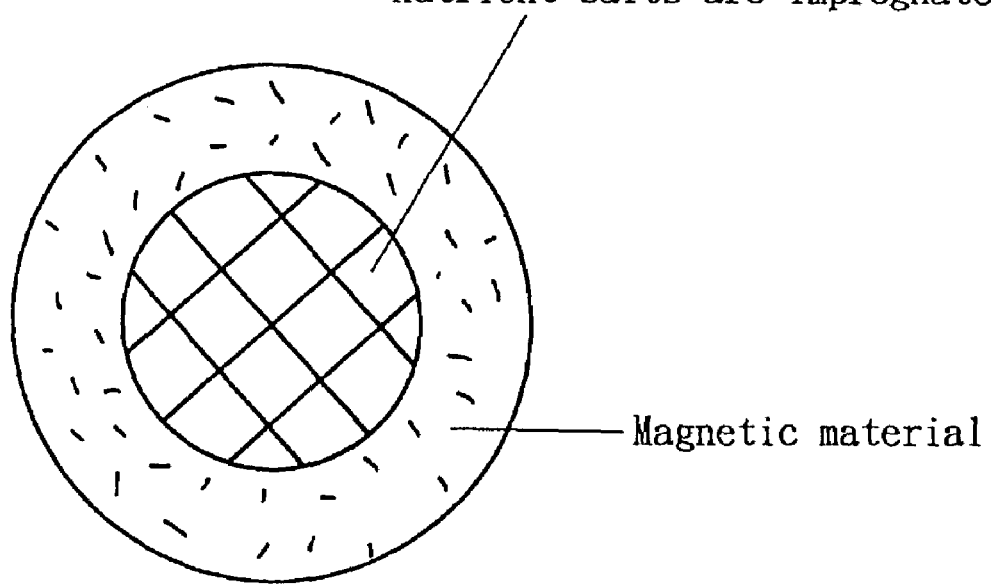
FIG. 8 is a drawing which shows an example having a magnetic coat.

Incidentally, in the carrier of this invention coated with a high-molecular polymer, magnetic powder such as ferrite may be dispersed and contained in the polymer so that control of transfer of the carrier by magnetism from outside is made possible. FIG. 8 is an exemplification of such an example as a model.

Figure 9:
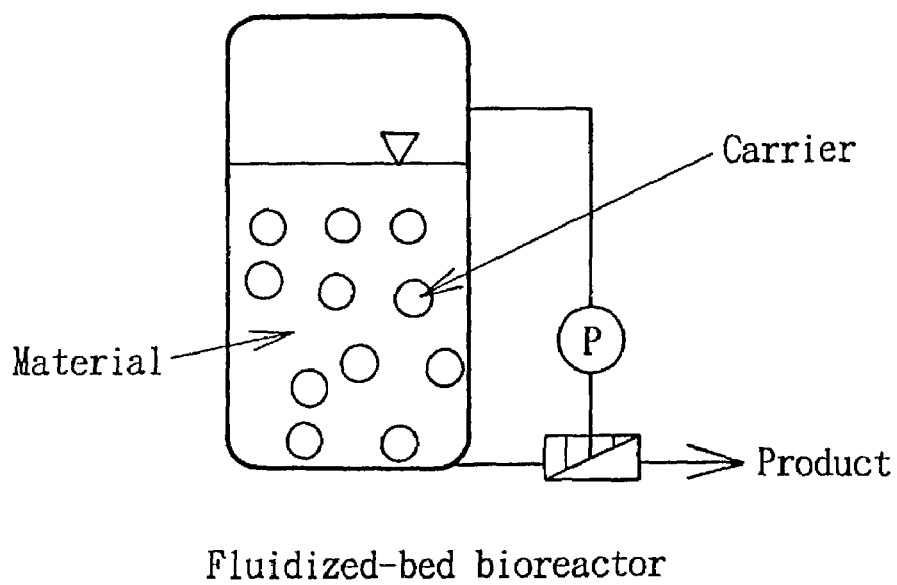
FIG. 9 is a drawing which shows an example of a fluidized-bed bioreactor.
Figure 10:
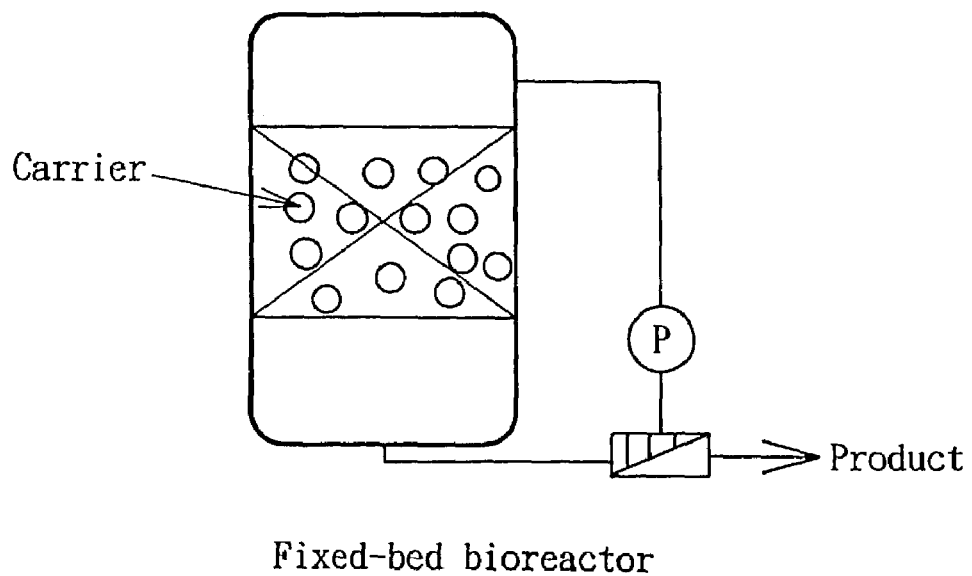
FIG. 10 is a drawing which shows an example of a fixed-bed bioreactor.
Figure 11:
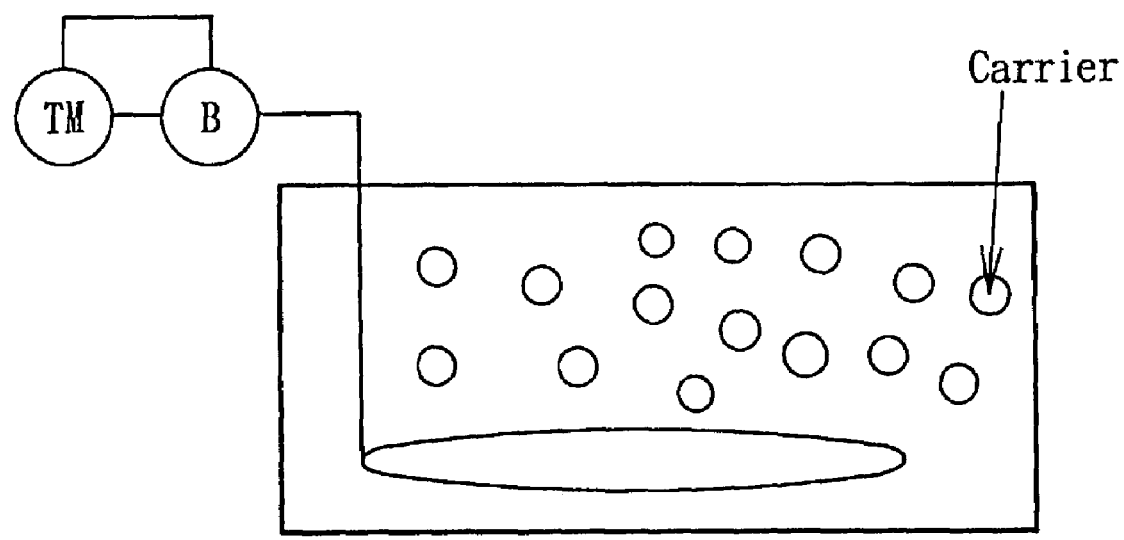
FIG. 11 is a drawing which shows an example of an apparatus for an intermittently aerative nitration and denitration.

FIG. 9 to FIG. 11 are examples where the carrier of this invention is used as a reactor, etc.

In case of treatment of waste water, a word-of "reactor" showned in FIGS. 9 and 10 means "degraded product".

By the use of the carrier of this invention, the microorganism concentration can be expected, for example, to be 20~40 g dry cells/liter. In conventional methods, that is around 1~5 g dry cells/liter.

In a decomposing system such as in the case of a waste water treatment, the decomposition can be expressed as follows wherein S is an amount of the substrate.

$$(dS/dt) = -\mu \cdot X/Y_{x/s}$$

In the formula, $\mu$ is a specific rate of proliferation of the microorganism; X is density of the microorganism; and $Y_{x/s}$ is a yield of the microorganism (this is a definite value for each microorganism).

In accordance with this invention, $\mu$ is actually operative at the region near $\mu_{max}$ and, therefore, the microorganism density X can be made 8~20-fold higher as compared with the conventional method. Thus, the decomposing rate in the apparatus for suspension culture increases in an exponential manner to an extent of 50~200-fold and it is now possible to increase to an extent of several times as compared with the bioreactor utilizing the conventional carriers.

Regarding this invention, it is considered that a porous material increases a density of microorganism in the are of pores. Especially, it is emphasized that a rock wool as an inorganic porous material works effectively as a carrier for a fixed-bed type methane fermentation process.

EXAMPLES

Example 1

Figure 12:
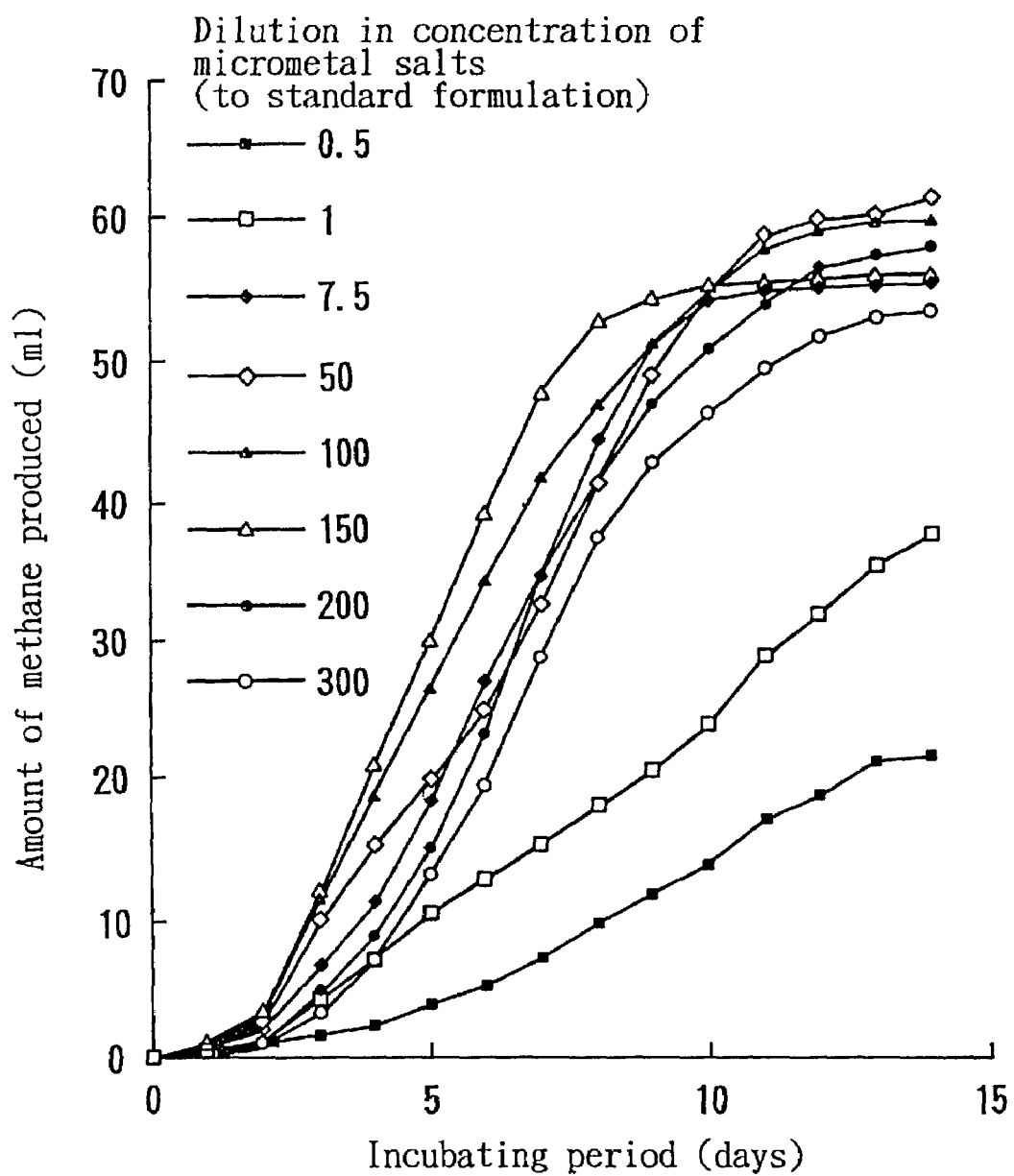
FIG. 12 is a graph which shows an example of results of methane production as a working example.

The attached FIG. 12 shows a relation to the formulation concentration when incubation of methane bacteria was conducted using a carrier where microelements and metal salts as the inorganic nutrient salts were carried on a PVA (polyvinyl alcohol) polymer gel obtained by dissolving PVA (weight average molecular weight being about 2,000 and degree of saponification being 98%) in water to an extent of about 16% by weight followed by subjecting to a cross-linking with saturated boric acid. The following Tables 1, 2 and 3 show compositions of metal elements in small amounts, basal inorganic salts and vitamin solutions, respectively.

TABLE 1

| Component | Concentration (µg/liter) |
|---|---|
| $MgCl_2.6H_2O$ | 410 |
| $MnCl_2.4H_2O$ | 50 |
| $FeCl_3.4H_2O$ | 50 |
| $NiCl_2.6H_2O$ | 12 |
| $ZnSO_4.7H_2O$ | 10 |
| $CaCl_2.2H_2O$ | 10 |
| $CoCl_2.6H_2O$ | 10 |
| $Na_2SeO_3$ | 8 |
| $Na_2MoO_4.7H_2O$ | 2.4 |
| $CuSO_4.5H_2O$ | 1 |
| $AlK(SO_4)_2$ | 1 |
| $H_3BO_4$ | 1.8 |
| $NaWO_4.2H_2O$ | 1 |

TABLE 2

| Component | Concentration (mg/liter) |
|---|---|
| $KH_2PO_4$ | 3400 |
| $K_2HPO_4$ | 3400 |
| $NH_4Cl$ | 2130 |
| $Na_2CO_3$ | 2540 |
| Resazurin | 2 |

TABLE 3

| Components | Concentration (µg/liter) |
|---|---|
| Biotin | 20 |
| Folic acid | 20 |
| Pyridoxine hydrochloride | 100 |
| Thiamine hydrochloride | 50 |
| Riboflavin | 50 |

TABLE 3-continued

| Components | Concentration (µg/liter) |
|---|---|
| Nicotinic acid | 50 |
| Calcium DL-pantothenate | 50 |
| p-Aminobenzoic acid | 50 |
| Lipoic acid | 50 |

It is noted therefrom that, when the formulation concentration is 150-fold of the conventional one, the speed for methane production increases to an extent of about 3.7-fold whereby the excellent function and merit of this invention can be ascertained.

Figure 13:
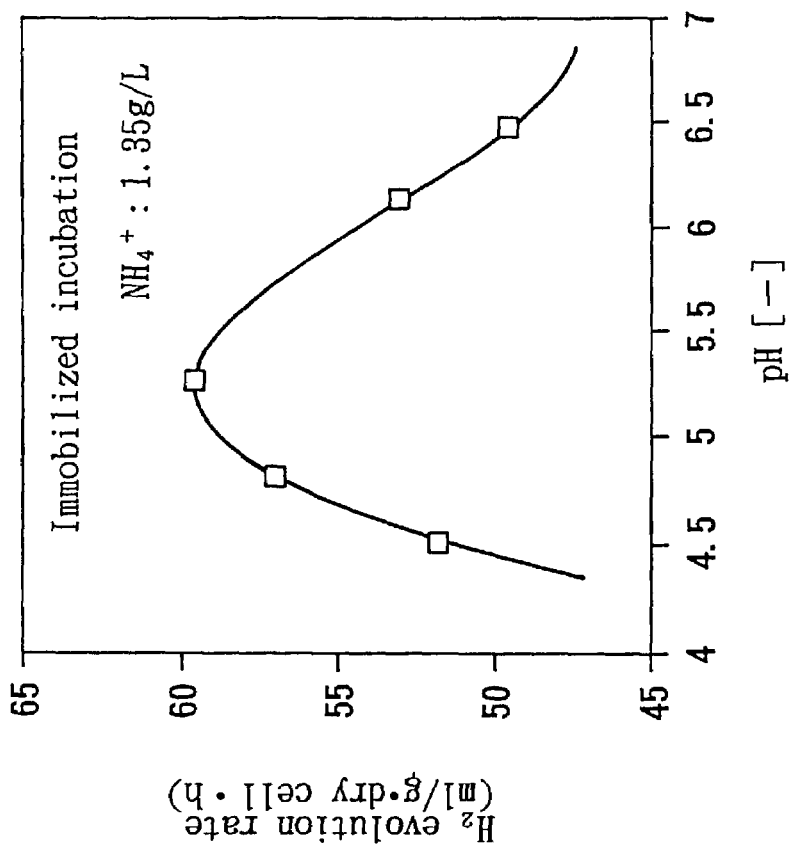
Figure 13:
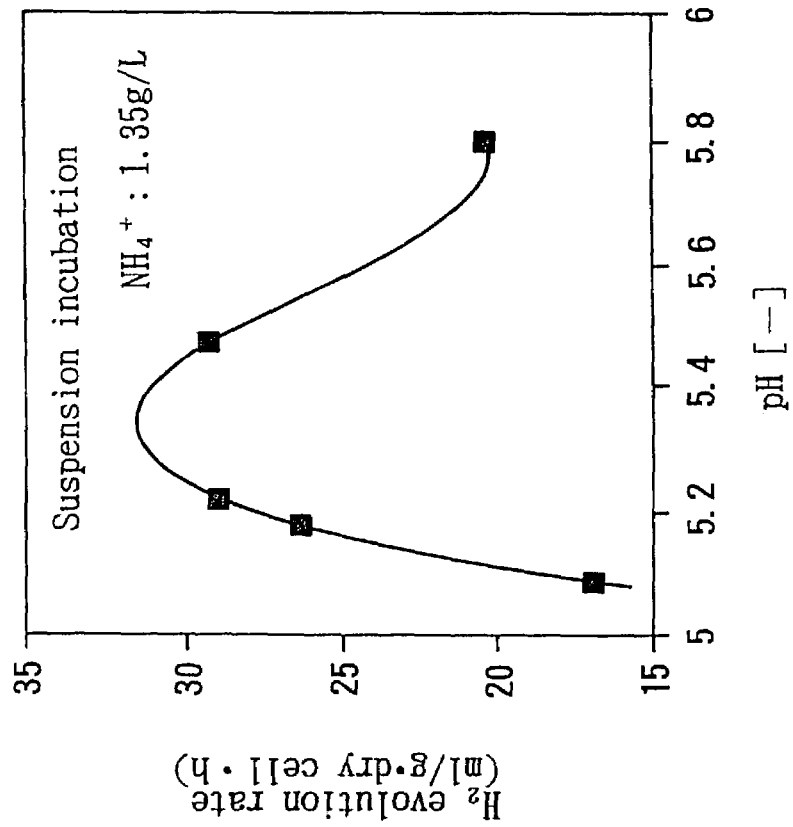

FIG. 13 shows the result in an experiment of hydrogen generation by said hydrogen-productive microorganism in a treatment of waste water having a very high $NH_4^-$ (ammonium) concentration in which the immobilized incubation of a hydrogen-productive microorganism (*Enterobacter aerogenes*) using the carrier of this invention is compared with the suspension incubation of the hydrogen-productive microorganism using no carrier. Proliferation of the hydrogen-productive microorganism is apt to be inhibited by nitrogen in a state of ammonia. The above is a result of the comparison by checking the allowable range of pH for checking that. The allowable pH range of the hydrogen-productive microorganism using the carrier is very broad as compared with the case of the suspension incubation. Although the optimum pH is 5.2~5.3 and is same in both cases but, at that pH value, the hydrogen-producing speed of the former case is about two-fold of the latter case whereby the merit of this invention is duly noted.

As fully illustrated hereinabove, the invention of this application is able to achieve high activity and high density of the microorganism in a bioreactor or in an apparatus for treating the waste water and, therefore, an improvement in ability of various bioreactors such as fluidized-bed and fixed-bed incubating apparatuses is ahieceved. In addition, when the carrier is utilized in conservation of environment such as in an ecological system, it is now possible to repair the deteriorated environment and to improve the repairing speed.

Example 2

Rock wool (made by Nitto Boseki Co.) which was molded to have a cylindrical shape (120 mm in diameter and 70 mm in height) and whose apparent volume was 0.8 liters (equal to 32 percent of liquid volume) was placed in a cylindrical glass fermentation tank whose total and liquid volumes were 3 and 2.5 liters, respectively. To compare the performance of this fixed-bed methane fermentation tank with that of a complete mixing methane fermentation tank, a complete mixing methane fermentation tank whose dimension was the same as above but which contained no rock wool was also installed.

Rock wool which was commonly used for hydroponics was used as the material for the fixed bed. Table 4 shows the physical properties of this rock wool. In a preliminary experiment, from the results which were obtained by measuring the volume of water until the seepage from the rock wool no longer occurred, it was found that the volume of water taken out from synthetic wastewater as the free water reached as high as 83% (v/v).

TABLE 4

Physical properties and composition of rock wool

| | |
|---|---|
| Density (kg/m$^3$) | 80 ± 12 |
| True specific gravity | 2.9 |
| Void ratio (%) | 97 |
| Composition (%) | $SiO_2$; 42, $Al_2O_3$; 15, CaO; 33, MgO; 6, Fe; 0.5; $TiO_2$; 0.9, MnO; 0.2, $Na_2O$; 1, $K_2O$; 0.8 |

As shown in Table 5, inorganic salts containing small amounts of metallic salts and vitamins were dissolved in distilled water and the resulting solution was sterilized in an autoclave (at 121° C. for 15 minutes). To this solution, acetic acid was added according to the acetic-acid load of fermentation tank. The solution thus prepared was used as synthetic wastewater for methane fermentation.

TABLE 5

Composition of substrate

| Component | Concentration (mg/L) | Component | Concentration (mg/L) |
|---|---|---|---|
| $NH_4HCO_3$ | 3000 | ReSaZurin | 1.000 |
| $K_2HPO_4$ | 450 | Vitamin $B_1$ | 0.100 |
| $(NH_4)_2SO_4$ | 450 | $Alk(SO_4)_2.12H_2O$ | 0.100 |
| $MgSO_4.7H_2O$ | 210 | $CuSO_4.5H_2O$ | 0.100 |
| NaCl | 900 | $H_2BO_3$ | 0.100 |
| $KH_2PO_4$ | 450 | Vitamin $B_6$ | 0.100 |
| $Na_2CO_3$ | 320 | Niacin | 0.050 |
| $CaCl_2.2H_2O$ | 120 | Thioctic acid | 0.050 |
| Cysteine.HCl | 250 | Folic acid | 0.020 |
| $Na_2S.9H_2O$ | 250 | Vitamin $B_2$ | 0.050 |
| $FeSO_4.7H_2O$ | 21 | P-aminobenzoic acid | 0.050 |
| $N(CH_3COOH)_2$ | 15 | Biotin | 0.020 |
| $ZnSO_4.7H_2O$ | 1 | Vitamin $B_{12}$ | 0.005 |
| $MnSO_4.5H_2O$ | 5 | $NiCl_2.6H_2O$ | 0.030 |
| $CoCl_2.6H_2O$ | 1 | $Na_2MoO_4.2H_2O$ | 0.100 |
| Yeast extract | 2 | | |

To the digested sludge collected from a digestion tank of Tsuchiura City's sewage treatment plant, synthetic wastewater containing acetic acid with a concentration of 5 g/l was semicontinuously added at a rate of once a day according to the draw & fill method. At the same time, the hydraulic retention time (HRT) was shortened from the initial 30 hours to 16 hours and the acclimation of sludge kept in a fermentation tank with a liquid capacity of 2.5 liters was carried out for about 6 months at 35 degrees C. Confirming the stable generation of methane gas due to acclimated methane bacteria, the sludge was observed using a phase-contrast & fluorescence microscope (BX50 made by Olympus). As a result, it was found that the bacteria belonging to the genus of *Methanosarcina* and *Methanothrix* were dominant. Therefore, it was decided to use these bacteria as the seeding bacteria for the start-up of methane-fermentation tank.

The above-mentioned fixed-bed methane fermentation and complete mixing methane fermentation tanks were installed in a water bath kept at 35° C. Under the same conditions as to the initial amount of seed, acetic-acid load and the average hydraulic retention time, these two methane fermentation tanks were started at the same time.

1) Start-up: First of all, the air existing in the gas phase of fermentation tank was replaced with $N_2$ gas to make the space oxygen free. Then, synthetic wastewater whose pH value was adjusted to neutral with 1-N hydrochloric acid and 2,250 ml of substrate containing no acetic acid were added to the fermentation tank. After that, 250 ml of the above seed bacteria solution were added anaerobically to the solution. From the 3rd day after this seeding, synthetic wastewater containing acetic acid was continuously fed into the fermentation tank. The feeding rate was gradually increased. In this way, the targeted acetic-acid load and HRT were achieved two weeks later.

2) Continuous operation experiment: After the methane generation rate in the fermentation tank reached the steady state, the characteristics of the fermentation tank which is operating in the period of more than twice of HRT were examined. Table 6 shows the operational conditions. As the indicators to judge whether the fermentation tank has reached the steady state, the volatile suspended organic substance density (MLVSS) which was considered as the density of bacteria in fermentation tank, the concentration of acetic acid and the gas generation rate were used.

TABLE 6

Operational conditions of both the fixed-bed and complete mixing methane fermentation tanks

| RUN | HRT (day) | Acetic-acid load (g/l.day) | Operation time (day) |
|---|---|---|---|
| 1 | 16.0 | 0.54 | 32 |
| 2 | 16.0 | 2.50 | 32 |
| 3 | 16.0 | 5.00 | 32 |
| 4 | 16.0 | 7.00 | 32 |
| 5 | 5.0 | 0.54 | 15 |
| 6 | 5.0 | 2.50 | 15 |
| 7 | 5.0 | 5.00 | 15 |
| 8 | 5.0 | 7.00 | 15 |
| 9 | 1.0 | 0.54 | 10 |
| 10 | 1.0 | 2.50 | 10 |
| 11 | 1.0 | 5.00 | 10 |
| 12 | 1.0 | 7.00 | 10 |
| 13 | 0.5 | 0.54 | 10 |
| 14 | 0.5 | 2.50 | 10 |
| 15 | 0.5 | 5.00 | 10 |
| 16 | 0.5 | 7.00 | 10 |

1. Relationship Between the Removal Rate of Acetic Acid and Dilution Rate

Figure 14:
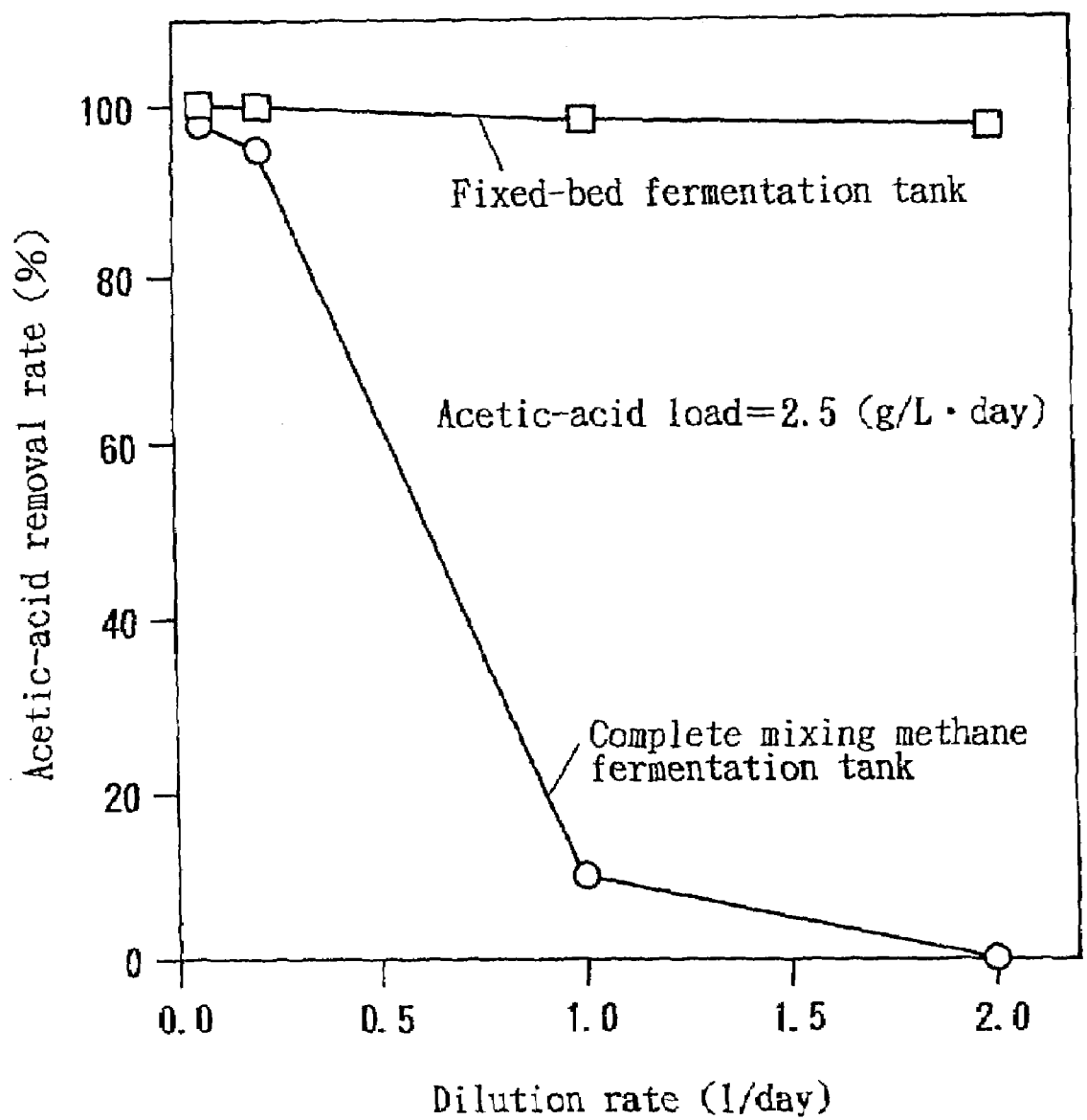
FIG. 14 is a drawing which shows the relationship between the removal rate of acetic acid and the dilution rate when the acetic acid load is 2.5 (g/L·day) in case of methane fermentation.

FIG. 14 shows the relationship between the removal rate of acetic acid and the dilution rate when the acetic-acid load is 2.5 (g/L·day). In an experiment where the fixed-bed methane fermentation tank was operated with a dilution rate of 1 (1/day), acetic acid was removed almost 100 percent. On the contrary, the fermentation in the complete mixing methane fermentation tank reached to a state of almost standstill. With a dilution rate of 2 (1/day), too, the removal rate of acetic acid in the fixed-bed methane fermentation tank was more 85 percent. This high removal rate is considered to have been achieved by the fact that the rock wool in the fixed-bed methane fermentation tank could fix many bacteria and therefore the microbe retention time (MRT) became longer than the average hydraulic retention time (HRT). That is, the wash-out preventative effect of rock wool is thought to be significant.

2. Relationship Between Acetic-Acid Removal Rate and Acetic-Acid Load

Figure 15:
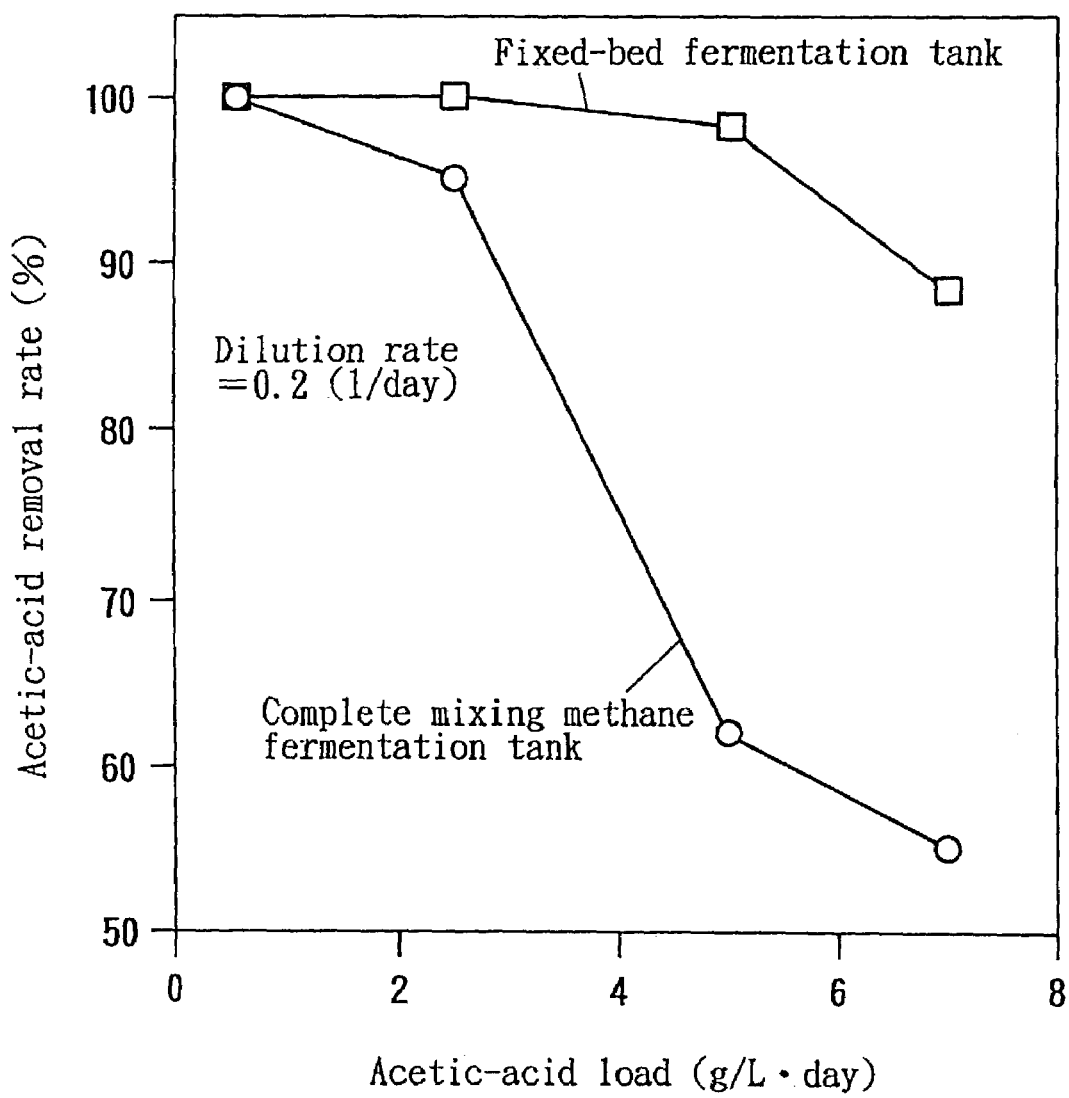
FIG. 15 shows the relationship between the acetic acid removal rate and the acetic acid load.
Figure 16:
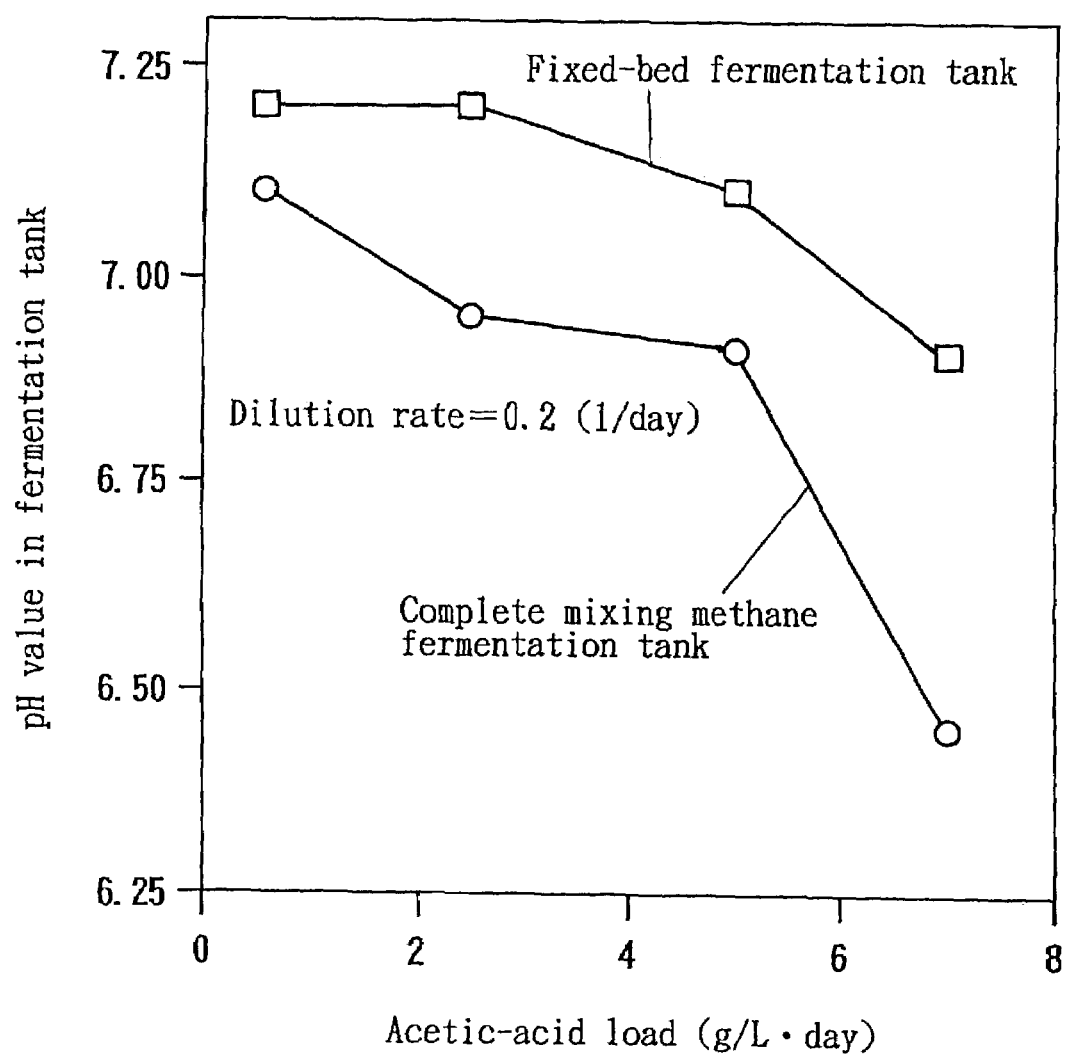
FIG. 16 shows the relationship between the pH value of the fixed-bed methane fermentation tank and the acetic acid load.
Figure 17:
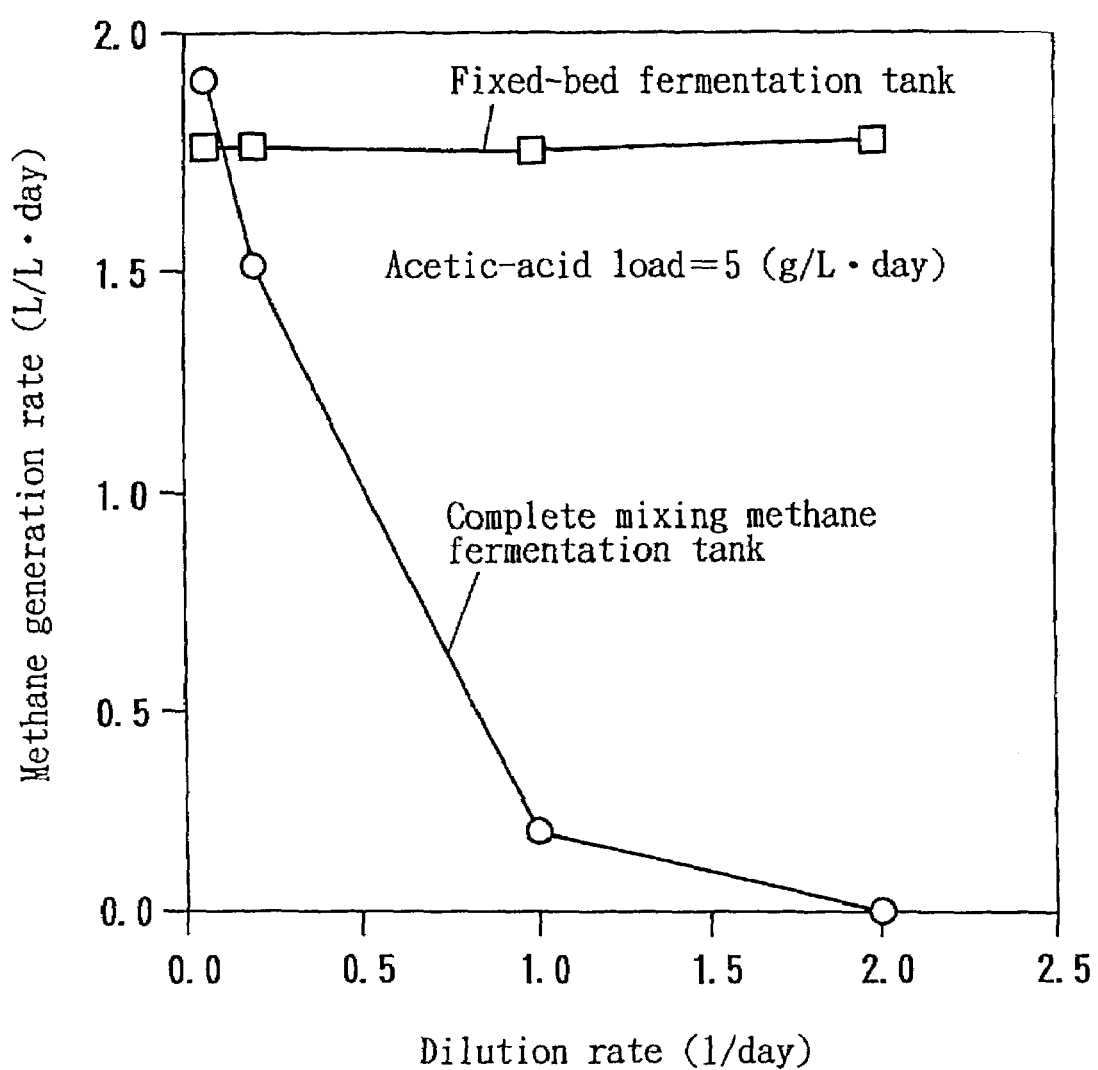
FIG. 17 is a drawing which shows the relationship between the methane generation rate and dilution rate.

FIG. 15 shows the relationship between the acetic-acid removal rate and the acetic-acid load when the dilution rate is 0.2 (l/day). The decrease in the acetic-acid removal rate of the fixed-bed methane fermentation tank was small until the level of acetic-acid load reached to 5 (g/L·day). Even with an acetic-acid load of 7 (g/L·day), the fixed-bed methane fermentation tank was able to achieved an acetic-acid removal rate of 88%. On the other hand, the acetic-acid removal rate of the complete mixing methane fermentation tank is greatly affected by the. For example, when the level of acetic-acid load is increased from 0.64 to 2.5 (g/L·day), the acetic-acid removal rate of the fixed-bed methane fermentation tank stayed almost at 100% while that of the complete mixing methane fermentation tank dropped to 95%. In addition, when the level of acetic-acid load is increased from 2.5 to 7 (g/L·day), the acetic-acid removal rate of the fixed-bed methane fermentation tank dropped from 98 to 88% while that of the complete mixing methane fermentation tank dropped from 95 to 52%. This large difference between the two tanks is considered to have been caused by the following reasons. That is, as the density of bacteria trapped in the fixed bed was kept at high levels, the decomposition of acetic acid was promoted in the fixed-bed methane fermentation tank. At the same time, the change in pH value of the fixed-bed methane fermentation tank due to changing acetic-acid load was smaller than that in the complete mixing methane fermentation tank as shown in FIG. 16. In a preliminary experiment, it was found that the pH and total alkalinity of fermentation liquid containing rock wool increased by about 0.2 and 50 ($CaCO_2$ mg/L) compared with the fermentation liquid containing no rock wool. Therefore, rock wool was considered to have the buffering effect on the change in the pH value of fermentation liquid due to changing acetic-acid load. 0.3. Relationship between methane generation rate and dilution rate FIG. 17 shows the relationship between the methane generation rate and dilution rate when the acetic acid load is 5 (g/L·day). When the dilution rate was increased from 0.06 to 2 (l/day), the decrease in the methane generation rate of the fixed-bed fermentation tank was small. On the other hand, the decrease in the methane generation rate of the complete mixing methane fermentation tank was only slightly larger than that of the fixed-bed fermentation tank when the dilution rate was below 0.21 (l/day). However, its decrease was drastic at a dilution rate over 0.2 (l/day). As is apparent from FIG. 18, the dilution rate at which the maximum bacterial density was achieved is 0.2 in the complete mixing methane fermentation tank and 1 in the fixed-bed methane fermentation tank. If the corresponding methane generation rates are compared, it becomes apparent that the methane generation rate of the fixed-bed methane fermentation tank incorporating rock wool is respectively 1.2 and 8.5 times higher than that of the complete mixing methane fermentation tank. This is perhaps indicating that the rock wool is preventing the "wash-out" of methane bacteria by firmly holding the methane bacteria in the rock wool.

4. Relationship Between the Density of Bacteria and Dilution Rate

Figure 18:
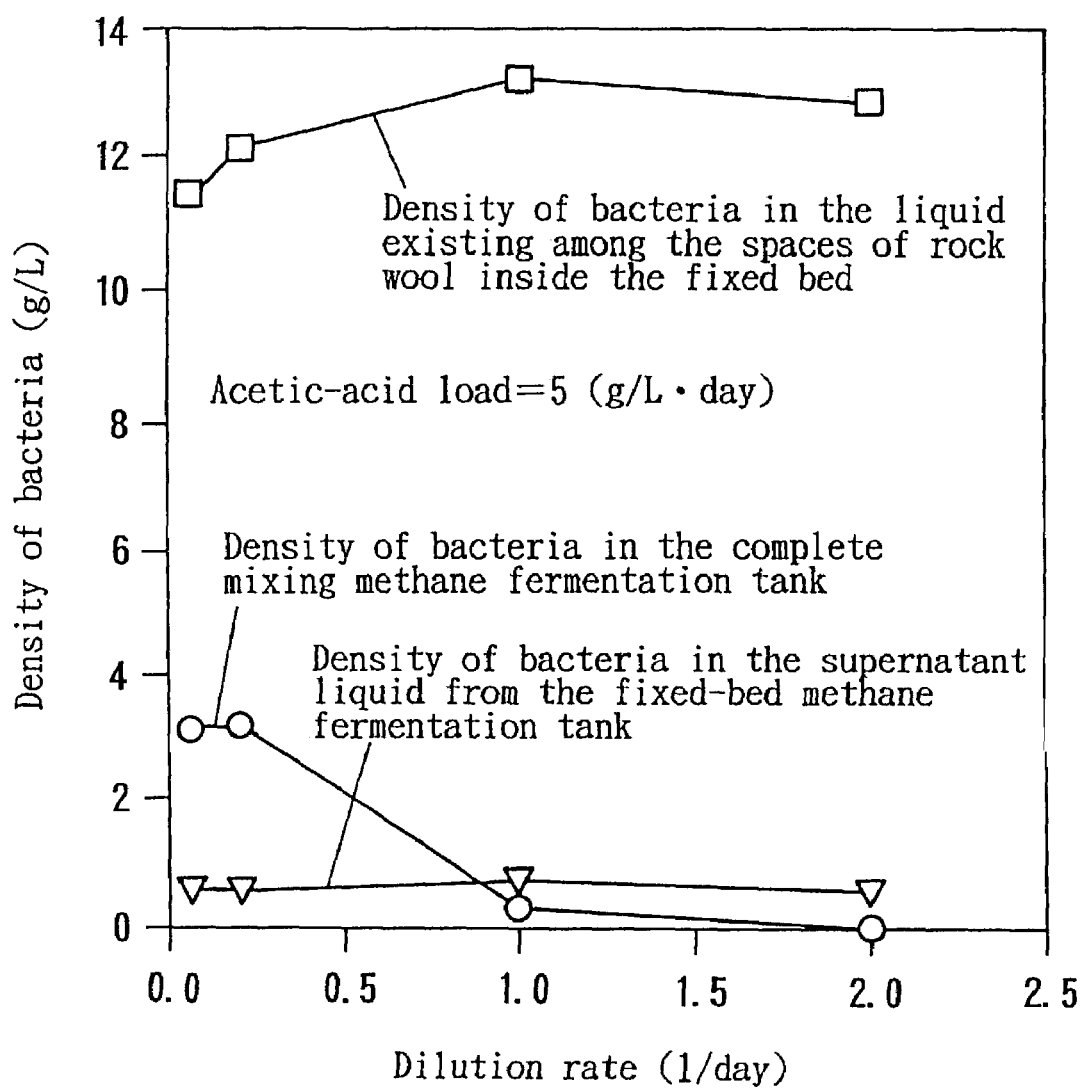
FIG. 18 is a drawing which shows the relationship between the density of bacteria (microorganism) and dilution rate.

FIG. 18 shows the relationship between the density of bacteria and dilution rate when the acetic-acid load is 5 (g/L·day) When the dilution rate was increased from 0.06 to 1 (l/day), the density of bacteria in the liquid existing among the spaces of rock wool increased to 13.2 (g/L). When the dilution rate was increased from 2 (l/day), the density of bacteria in the liquid existing among the spaces of rock wool slightly decreased to 12.2 (g/L). However, the density of bacteria in the supernatant liquid from the fixed-bed fermentation tank did not change much or 0.8 (l/day). In the case of the complete mixing methane fermentation tank, meanwhile, when the dilution rate was increased from 0.06 to 0.2 (l/day), the density of bacteria in the tank increased from 3.1 to 3.3 (g/L). At a dilution rate over 0.2, the density of bacteria in the tank decreased markedly or 0.2 (g/L) at a dilution rate of 1 (l/day) and 0.0 (g/L) at a dilution rate of 2 (l/day). These facts suggest that the rock wool in the fixed-bed methane fermentation tank is preventing the "wash-out" of large amounts of methane bacteria and that in the complete mixing methane fermentation tank the "wash-out" of methane bacteria occurs when the dilution rate exceeds 0.2 (l/day).

Here, the average methane bacterial density for the effective volume of the fixed-bed methane fermentation tank when the dilution rate was 1 (l/day) was as follows: 0.32×13.50+(1−0.32)×1=5.00 (g/L). This is 1.5 times higher than the density of bacteria 3.3 (g/l) found in the complete mixing methane fermentation tank when the dilution rate is 0.2 (l/day), indicating how excellent the rock wool's ability of holding methane bacteria is.

5. Relationship Between the Density of Bacteria and Acetic-Acid Load

Figure 19:
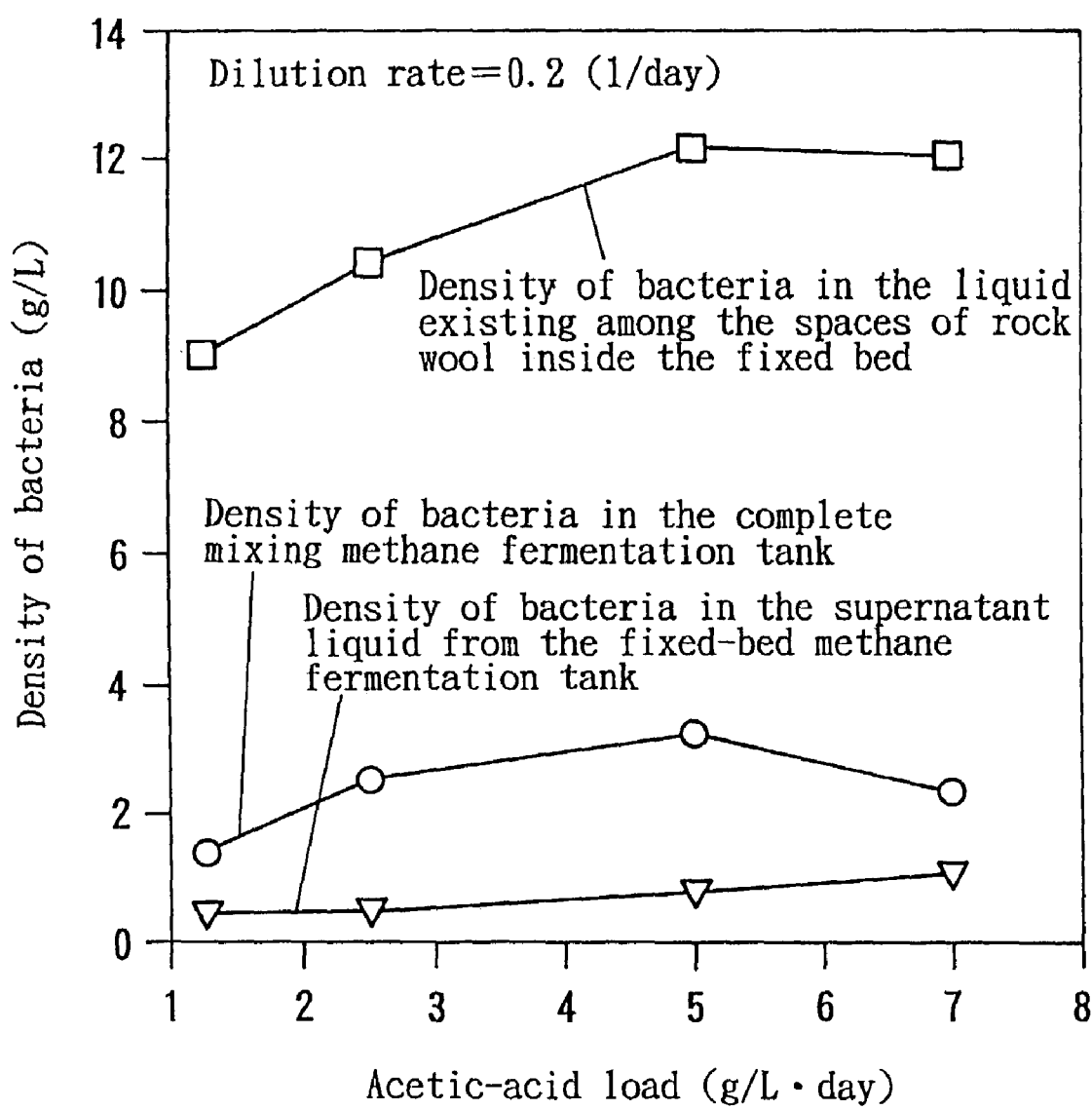
FIG. 19 shows the relationship between the density of bacteria (microorganism) and the acetic acid load.

FIG. 19 shows the relationship between the density of bacteria in the liquid existing in the fixed bed and in the supernatant liquid from the fixed-bed methane fermentation tank and the acetic-acid load as well as the relationship between the density of bacteria and acetic-acid load of the complete mixing methane fermentation tank when the dilution rate is 0.2 (l/day). From this figure, it is apparent that the bacterial density both in the liquid existing in the fixed bed and in the complete mixing methane fermentation tank increased until the level of acetic-acid load reached to 5 (g/L·day). However, when the level of acetic-acid load reached to 7 (g/L·day), the level of these bacterial-density values began to decrease. Here, the density of bacteria in the liquid existing in the fixed bbd was found to be about 8 times higher than that in the complete mixing methane fermentation tank.

Figure 20:
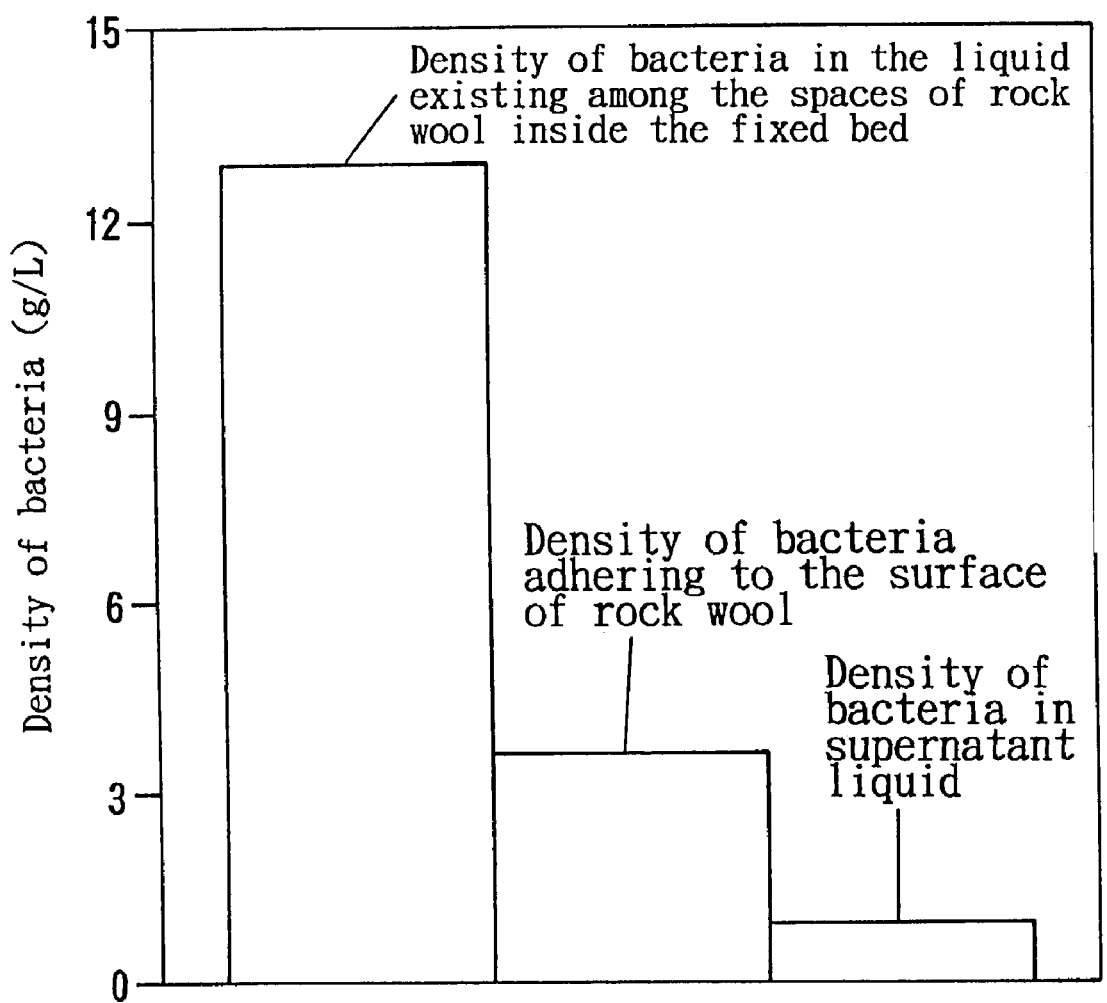
FIG. 20 shows the results of the density of bacteria (microorganism).

FIG. 20 shows the results of the density of bacteria Which was adhering to the surface of rock wool, existing in the liquid inside rock wool and found in the supernatant liquid from the fixed-bed methane fermentation tank immediately after the end of fermentation experiment conducted under harsh conditions acetic-acid load of 7 (g/L·day) and dilution rate of 2 (l/day) using the fixed-bed methane fermentation tank. Here, the density of bacteria adhering to the surface-of rock wool was calculated from the following formula (1) by using the density of bacteria washed out of fixed bed and the density of bacteria containing in the liquid inside fixed bed.

Density of bacteria adhering to the surface of rock wool (g/L)=(density of bacteria washed out of fixed bed−volume of liquid inside fixed bed× density of bacteria containing in the liquid inside fixed bed)/volume of fixed bed The density of bacteria containing in the liquid inside the fixed bed was about 4 times higher than the density of bacteria adhering to the surface of rock wool and about 12 times higher than the density of bacteria found in the supernatant liquid from the fixed-bed methane fermentation tank. In addition, although the color of rock wool as support has blackened until the experiment was completed, neither deformation nor break was observed in the rock wool. Thus, it was considered that rock wool was an inexpensive and durable material suitable for fixed bed.

In this case, it was found that the density of bacteria in a fermentation tank incorporating rock wool as support could be kept at high levels even when both the dilution rate and acetic-acid load were high because rock wool appeared to provide a good environment to methane bacteria where they could easily be trapped physically in the rock wool of fixed bed for their further growth. It was thought that this method was quite likely to lead to the realization of a high-speed methane-fermentation based on acetic-acid utilizing methane bacteria.

What is claimed is:

1. A carrier for microorganism incubation comprising a porous substrate consisting essentially of ceramic, natural stone or rock wool having microelements and inorganic nutrient salts diffused therein, which microelements and inorganic nutrients salts are useful for proliferation of the microorganism, and the surface of said carrier containing said microelements and inorganic nutrient salts diffused therein is coated with a high-molecular weight polymer to control diffusion of said microelements and inorganic nutrient salts.

2. The carrier for microorganism incubation according to claim 1 wherein organic carbon sources are included in said porous substrate.

3. The carrier for microorganism incubation according to claim 1 wherein a microorganism is included in the carrier.

4. The carrier for microorganism incubation according to claim 1 wherein said carrier includes microorganisms and is subjected to an enrichment proliferation of the microorganisms on the surface thereof and is further coated with the high-molecular weight polymer after said proliferation.

5. The carrier for microorganism incubation according to claim 1 wherein the carrier includes a biodegradable resin.

6. The carrier for microorganism incubation according to claim 1, wherein the high-molecular polymer coating contains magnetic powder.

7. The carrier for microorganism incubation according to claim 1 wherein the porous substrate is a ceramic or natural stone.

8. The carrier for microorganism incubation according to claim 1 comprising a rock wool as said porous substrate.

9. The carrier for microorganism incubation according to claim 4 wherein the further coated high-molecular weight polymer contains magnetic powder.

10. The carrier for microorganism incubation according to claim 2, wherein said carbon sources comprise glucose and/or biodegradable resin.

11. A process for fermentation to produce methane which comprises culturing a methane producing microorganism on a fixed bed comprising the carrier of claim 8.

* * * * *